United States Patent
Halstead et al.

(10) Patent No.: US 6,874,517 B2
(45) Date of Patent: Apr. 5, 2005

(54) VALVE HOLDING FIXTURE FOR AUTOMATED REPROCESSOR

(75) Inventors: Eric Halstead, Beauport (CA); Gerald E. McDonnell, Basingstoke (GB); Robert M. Priest, Eastlake, OH (US)

(73) Assignee: Steris Inc., Temecula, CA (US)

( * ) Notice: Subject to any disclaimer, the term of this patent is extended or adjusted under 35 U.S.C. 154(b) by 69 days.

(21) Appl. No.: 10/446,763

(22) Filed: May 28, 2003

(65) Prior Publication Data

US 2004/0238014 A1 Dec. 2, 2004

(51) Int. Cl.⁷ .................................................. B08B 3/04
(52) U.S. Cl. .............. 134/170; 134/169 R; 134/169 C; 422/292
(58) Field of Search ............................ 134/170, 166 R, 134/169 R, 169 C, 200; 422/291, 292, 300, 301

(56) References Cited

U.S. PATENT DOCUMENTS

| | | | | |
|---|---|---|---|---|
| 3,009,468 A | * | 11/1961 | Eberle ......................... | 134/93 |
| 3,375,834 A | * | 4/1968 | Best et al. .................. | 134/94.1 |
| 3,577,279 A | * | 5/1971 | Lightner ...................... | 134/23 |
| 4,130,444 A | * | 12/1978 | Anderka ..................... | 134/96.1 |
| 4,838,288 A | * | 6/1989 | Wright et al. ................ | 134/110 |
| 4,979,527 A | * | 12/1990 | Mueller et al. ........... | 137/15.06 |
| 5,090,433 A | * | 2/1992 | Kamaga .................. | 134/169 C |
| 5,293,960 A | * | 3/1994 | Majerowicz et al. ....... | 184/13.1 |
| 5,320,119 A | * | 6/1994 | Griffiths .................... | 134/95.1 |
| 5,402,810 A | * | 4/1995 | Donley ...................... | 134/135 |
| 5,524,656 A | * | 6/1996 | Konarski et al. ........... | 134/198 |
| 5,615,859 A | * | 4/1997 | Haag, III ................... | 251/61.1 |
| 6,041,797 A | * | 3/2000 | Casselman ................. | 134/152 |

* cited by examiner

Primary Examiner—Frankie L. Stinson
(74) Attorney, Agent, or Firm—Kusner & Jaffe; Michael A. Centanni

(57) ABSTRACT

A fixture for holding a valve assembly in an automated washing system, wherein the valve assembly is movable between an opened position and a normally closed position. The fixture is comprised of first and second housing sections that are releaseably attachable to each other. The housing sections define an internal cavity that is dimensioned to hold the valve assembly in an opened position. A fluid inlet is in communication with the chamber, and is attachable to a source of an anti-microbial fluid in the washing system. A fluid outlet communicates with the chamber to allow the anti-microbial fluid to exit the fixture.

24 Claims, 4 Drawing Sheets

US 6,874,517 B2

VALVE HOLDING FIXTURE FOR AUTOMATED REPROCESSOR

FIELD OF THE INVENTION

The present invention relates generally to the field of disinfection or sterilization of medical, dental, pharmaceutical or mortuary objects and devices, and more particularly to disinfection and sterilization of flexible endoscopes and parts and fittings therefore.

BACKGROUND OF THE INVENTION

An endoscope is an instrument equipped with a lighting and lens system used typically by physicians for visual examination of the interior of a body organ or cavity. Endoscopes include valves that are used by the physician to open and close air/water channels and suction/biopsy channels in the endoscope. During an endoscopic procedure, the instrument becomes coated with blood and other protein-rich body fluids, requiring that the endoscope undergo a thorough cleaning and anti-microbial deactivation between each use. Liquid microbial deactivation systems are now widely used to clean and deactivate equipment, such as endoscopes, that could not withstand the high temperatures of a steam sterilization system. Liquid microbial deactivation systems typically operate by exposing surfaces of the endoscope to a liquid disinfectant or sterile composition, such as peracetic acid or some other strong oxidant.

A problem with such systems is that they cannot adequately clean and deactivate the valves used within the endoscope. In this respect, endoscope valves are typically movable between a first normally closed position, wherein a surface on one valve component is "seated" against a surface on another valve component and a second open position, wherein the respective surfaces of the components are spaced from each other. When the valve is removed from the endoscope, these surfaces are normally biased into contact with each other, thereby preventing the liquid disinfectant or sterilant composition from contacting and deactivating such surfaces.

One method of cleaning such valve assemblies is to physically, i.e., manually, separate the contacting surfaces and expose the surfaces to the disinfectant or sterilant composition. Such a process is undesirable in that it requires an operator to physically handle the valve assembly and thus be exposed to any contamination thereon. Moreover, such a cleaning process is subjected to human error, and it is difficult to establish the efficacy of such a cleaning process.

Other proposed methods of cleaning the valve assemblies include sonic cleaning or re-processing in an automated system using bags, baskets, or multiple processed cycles.

None of these methods of cleaning guarantees that the contacting surfaces of the valve assemblies are separated from each other, and are thoroughly exposed to the cleaning and disinfecting solution during a reprocessing operation. Moreover, reprocessing that requires special or repeated cleaning and disinfecting cycles is not economically desirable to a customer.

The present invention overcomes these and other problems and provides a fixture for holding a valve assembly in an automated reprocessor system, wherein the valve assembly is maintained in an "opened" position exposing normally contacting surfaces to the cleaning and disinfecting solution during a reprocessing operation.

SUMMARY OF THE INVENTION

In accordance with a preferred embodiment of the present invention, there is provided a fixture for holding a valve component in a washing system. The valve component has an open position and a normally closed position. The fixture is comprised of a first housing section and a second housing section. The sections are releasably attachable to each other to form a fixture operable to hold the valve component in an opened position within the fixture. The first housing section has an internal cavity dimensioned to receive a portion of the valve component through a first opening therein. The first housing section also has a fluid opening therethrough in communication with the internal cavity. The fluid opening is dimensioned to receive an anti-microbial fluid therethrough. The second housing section has a second cavity dimensioned to receive a second portion of the valve component therein. The second housing has at least one fluid opening, and the first housing section is attachable to the second housing section with the first cavity in the first housing section in registry with the second cavity in the second housing section to define a valve fixture holding chamber dimensioned to receive and hold the valve component in said opened position. The holding chamber dimensioned to allow fluid to pass around and through the valve component when an anti-microbial fluid is forced through the valve fixture holding chamber through the openings in the first and second housing sections.

In accordance with another aspect of the present invention, there is provided a fixture for holding a valve assembly in an automated washing system. The valve assembly is movable between an opened position and a normally closed position. The fixture is comprised of a first housing section and a second housing section that are releaseably attachable to each other. The first housing section has a first internal cavity dimensioned to receive at least a portion of the valve component therein, and an opening communicating with the internal cavity. The second housing section is releaseably attachable to the first housing section. The second housing section forms a fluid-tight attachment with the first housing section. The first and second housing sections when attached to each other define an internal chamber that is dimensioned to receive and hold the valve assembly in an opened position and to define a space around valve assembly. A first opening in the first housing section connects to the source of an anti-microbial fluid to allow the chamber to be filled with the anti-microbial fluid.

In accordance with another aspect of the present invention, there is provided a fixture for holding a valve assembly in an automated washing system. The valve assembly is movable between an opened position and a normally closed position. The fixture is comprised of first and second housing sections that are releaseably attachable to each other. The housing sections define an internal cavity that is dimensioned to hold the valve assembly in an opened position. A fluid inlet is in communication with the chamber, and is attachable to a source of an anti-microbial fluid in the washing system. A fluid outlet communicates with the chamber to allow the anti-microbial fluid to exit the fixture.

In accordance with yet another aspect of the present invention, there is provided a method of cleaning a valve assembly from a medical instrument. The valve assembly is movable between an opened position, wherein normally contacting surfaces are spaced-apart and a normally closed position, wherein the normally contacting surfaces are in contact with each other. The method of cleaning comprises the steps of:

a) inserting a valve assembly into a fixture within a washing system, wherein the fixture is operable to hold the valve assembly in an opened position during a washing cycle; and b) forcing an anti-microbial fluid around and through the valve assembly during the washing cycle.

An advantage of the present invention is a means for cleaning a valve assembly that does not require operator exposure to the valve assembly during the cleaning and sterilization process.

Another advantage of the present invention is a fixture for cleaning a valve assembly from an endoscope or the like in an automated reprocessing system.

Another advantage of the present invention is a fixture for cleaning valve assemblies from an endoscope and the like that maintains the valve assembly in a position exposing all surfaces of the valve assembly to the cleaning and disinfecting solutions.

Another advantage of the present invention is a fixture for cleaning a valve assembly from an endoscope or the like that allows complete reprocessing of a valve assembly during a single, regular reprocessing operation.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
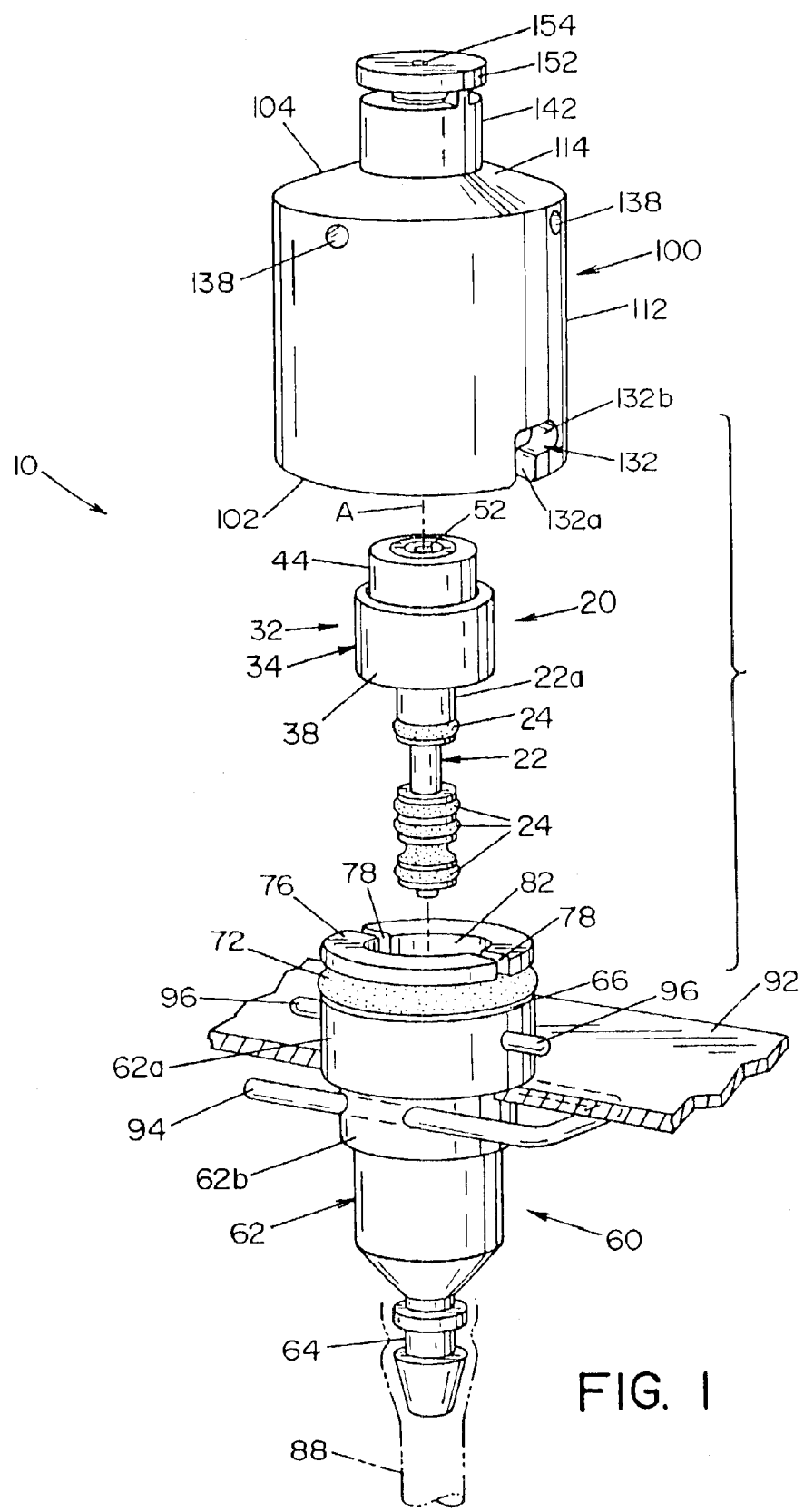
FIG. 1 is an exploded, perspective view of a valve assembly from an endoscope or the like and a fixture for holding the valve assembly in an automated reprocessor system, illustrating a preferred embodiment of the present invention.

Referring now to the drawings wherein the showings are for the purpose of illustrating the preferred embodiment of the invention only, and not for the purpose of limiting same, FIG. 1 shows a fixture 10 for supporting a valve assembly 20 from a medical instrument, such as an endoscope or the like, in an automated reprocessor, illustrating a preferred embodiment of the present invention.

Figure 2:
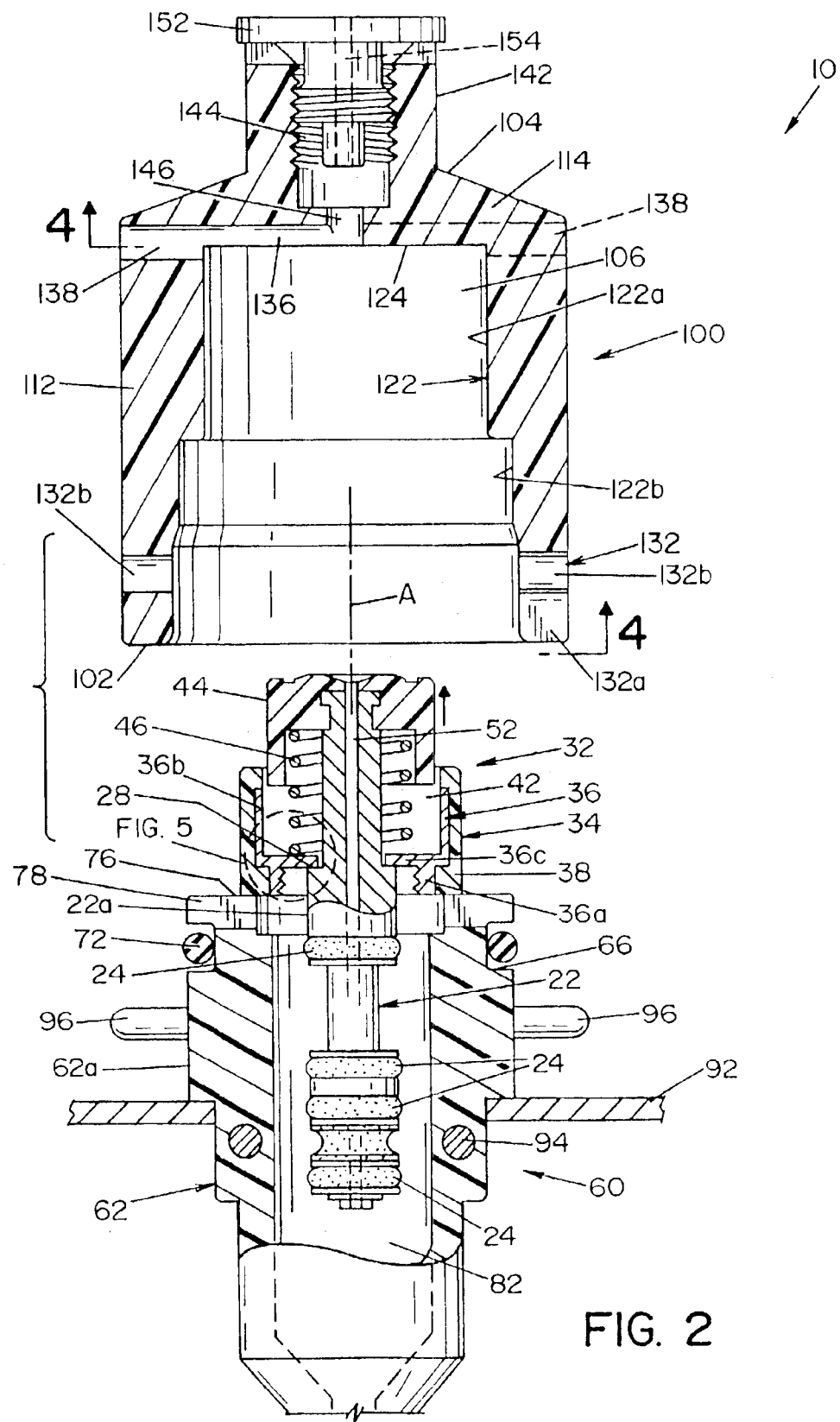
FIG. 2 is a cross-sectional view of the fixture shown in FIG. 1 in a disassembled state, illustrating two housing sections that form the fixture spaced-apart from each other, and a valve assembly in its normal configuration positioned within one of the housing sections.
Figure 3:
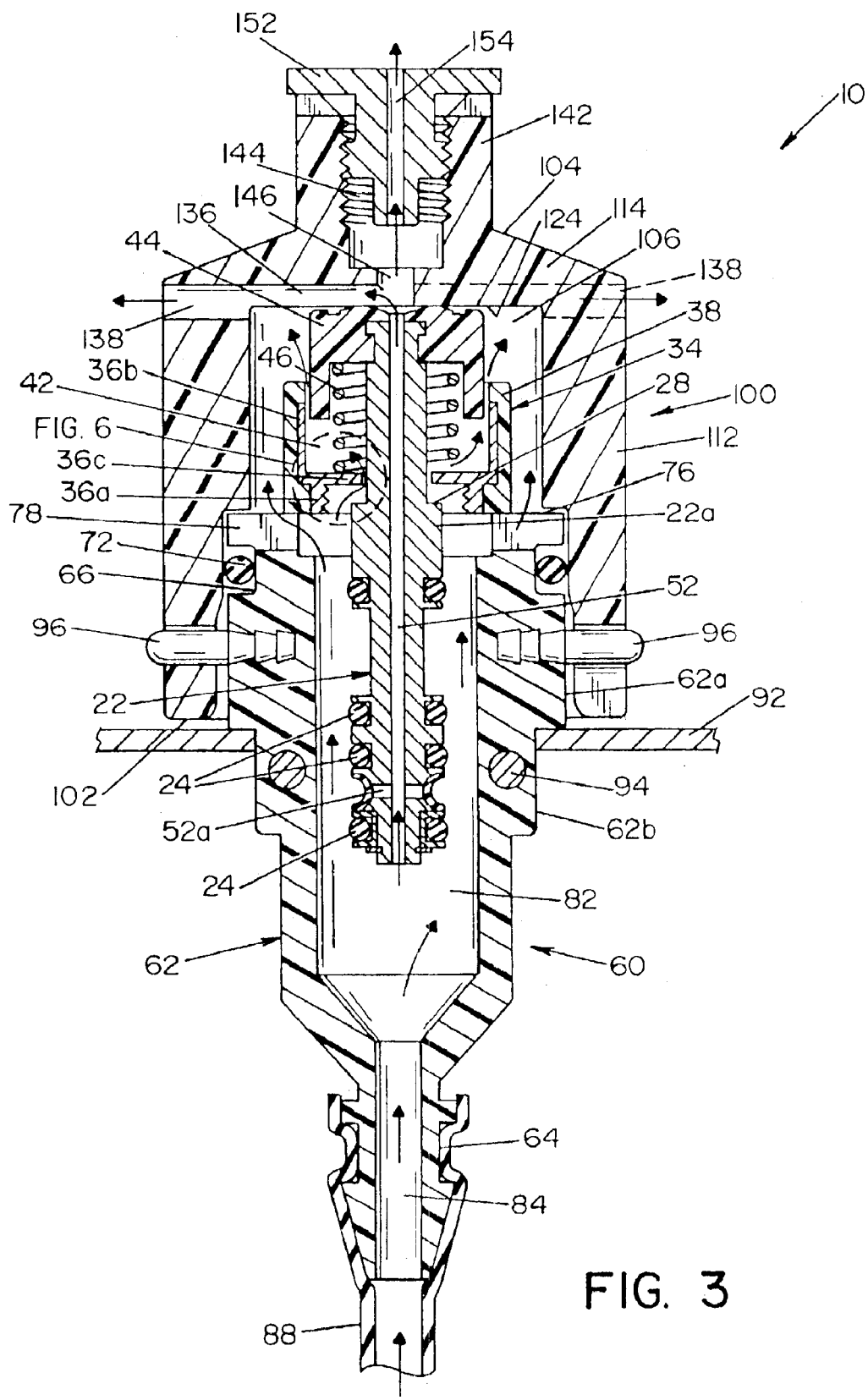
FIG. 3 is a cross-sectional view of the fixture shown in FIG. 1 in an assembled state with a valve assembly disposed therein.

Valve assembly 20 in and of itself forms no part of the present invention, but shall be described to provide a better understanding of fixture 10 and its operation. Valve assembly 20, as shown in the drawings, is representative of a typical valve assembly found in an endoscope or other similar medical devices. Valve assembly 20 is essentially comprised of an elongated valve stem 22 having a valve actuating assembly 32 at one end and a plurality of spaced-apart O-rings 24 at the other end. Valve actuating assembly 32, best seen in FIGS. 2 and 3, is basically comprised of a collar 34 that is adapted to attach valve assembly 20 to mating surface on an endoscope (not shown). Collar 34 is basically comprised of an inner metal sleeve 36 and an outer plastic jacket or casing 38. Metal sleeve 36 is generally cylindrical in shape and has a first end portion 36a and a second end portion 36b that are separated by an inwardly extending annular wall 36c. First end portion 36a of metal sleeve 36 includes internal threads that allow collar 34 to be attached to mating threads on a post or shoulder (not shown) on the endoscope. Second end portion 36b defines a cylindrical cavity 42 dimensioned to receive a cap or button 44 that is attached to one end of valve stem 22, as best seen in FIGS. 2 and 3. A biasing element 46, in the form of a helical spring, is disposed between cap 44 and annular wall 36c. Valve stem 22 includes an enlarged central portion 22a that defines an annular surface 28, best seen in FIGS. 5 and 6. Annular surface 28 abuts annular wall 36c to limit movement of valve stem 22 relative to collar 34, as best illustrated in FIGS. 2 and 5.

An elongated passage or lumen 52 extends axially through valve stem 22 and cap 44. Lumen 52 includes laterally extending branches 52a, as best seen in FIG. 3.

Figure 5:
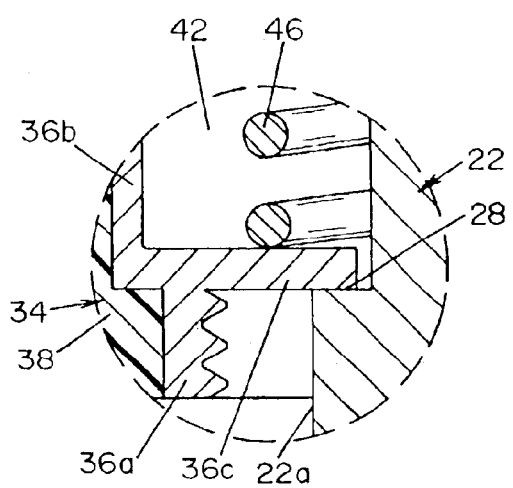
FIG. 5 is an enlarged view of the area designated FIG. 5 in FIG. 2.
Figure 6:
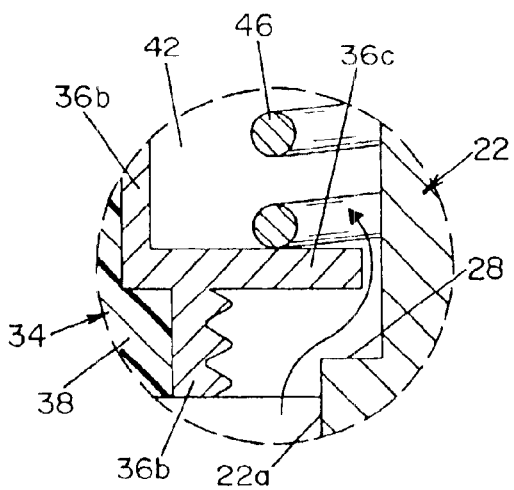
FIG. 6 is an enlarged view of the area designated FIG. 6 in FIG. 3.

Spring 46 biases valve stem 22 to a first position, as best seen in FIGS. 2 and 5, wherein annular surface 28 of central portion 22a abuts the surface of annular wall 36c.

Valve assembly 20 is part of an endoscope (not shown), and is attached thereto with valve stem 22 being positioned within a cylindrical bore within the endoscope. Fluid ports within the endoscope intersect the cylindrical bore, and are provided for controlling air or fluid flow within the endoscope. O-rings 24 on valve stem 22 are disposed relative to the ports such that movement of valve stem 22 relative to the ports opens or closes select ports within the endoscope, in a manner that is conventionally known.

Fixture 10 is adapted to hold valve assembly 20 during a cleaning cycle in an automated reprocessor. Fixture 10 is comprised of a first housing section 60 and a second housing section 100. In the embodiment shown, first housing section 60 is generally tubular in shape and includes a generally cylindrical body portion 62 that tapers down to a smaller end portion 64 that is shaped to define a tube fitting. Body portion 62 has an outer cylindrical surface 62a. An annular recess 66 is formed in surface 62a of cylindrical body portion 62. Recess 66 is dimensioned to receive an O-ring 72. Body portion 62 has a planar end surface 76. A transverse slot 78 is formed in end surface 76.

In the embodiment shown, first housing section 60 includes a cavity 82 dimensioned to receive a portion of valve assembly 20. In the embodiment shown, cavity 82 is cylindrical in shape and is dimensioned to receive valve stem 22 of valve assembly 20. As shown in the drawings, cavity 82 is accessible through end surface 76. In this respect, cavity 82 is dimensioned to be larger than valve stem 22 so as to define space therearound, but is smaller than collar 34, wherein collar 34 abuts end surface 76. An opening 84 through end portion 64 communicates with cavity 82. End portion 64 of the housing section is dimensioned to receive a conventional polymer tubing 88 (best seen in FIG. 3), as shall be described in greater detail below. A pair of pins 96 extend outwardly from body portion 62. Pins 96 are axially aligned with each other and extend from opposite sides of body portion 62. Body portion 62 includes a cylindrical portion 62b of reduced diameter to allow housing section 60 to be received within an opening in a mounting plate 92, as best seen in FIG. 1. A generally U-shaped pin 94 extending through holes in cylindrical portion 62b is operable to lock first housing section 60 to mounting plate 92.

Second housing section 100 is dimensioned to releaseably attach to first housing section 60. In the embodiment shown, second housing section 100 is generally cylindrical in shape and has an opened end 102 and a closed end 104. Second housing section 100 defines a generally cylindrical cavity 106 dimensioned to receive a valve actuating assembly 32 of valve assembly 20 and body portion 62 of first housing section 60. Second housing section 100 includes a cylindrical side wall portion 112 and an end wall portion 114. Side wall portion 112 includes an inner surface 122 and end wall portion 114 includes an inner surface 124, as best seen in FIG. 2. Inner surface 122 of side wall portion 112 is generally cylindrical in shape and includes sections of varying diameter. A first section 122a of inner surface 122 is cylindrical in shape and communicates with surface 124 formed by end wall portion 114. Surface section 122a and surface 124 define a generally cylindrical cavity for receiving collar 34 and button 44 of valve stem 22. Section 122b of inner surface 122 is dimensioned to engage O-ring 72 in first housing section 60 in fluid-type fashion.

A pair of L-shaped slots 132 are formed in second housing section 100, as best seen in FIG. 1. L-shaped slots 132 extend into side wall portion 112 from open end 102 of second housing section 100. L-shaped slots 132 include a first leg portion 132a that extends in a direction that is parallel to the central axis "A" of fixture 10, and a second leg portion 132b that extends at a right angle to first leg portion 132a, as best seen in FIG. 1. L-shaped slots 132 are dimensioned to receive pins 96 of first housing section 60, wherein second housing section 100 can be attached to first housing section 60 in a bayonet-locking fashion.

Figure 4:
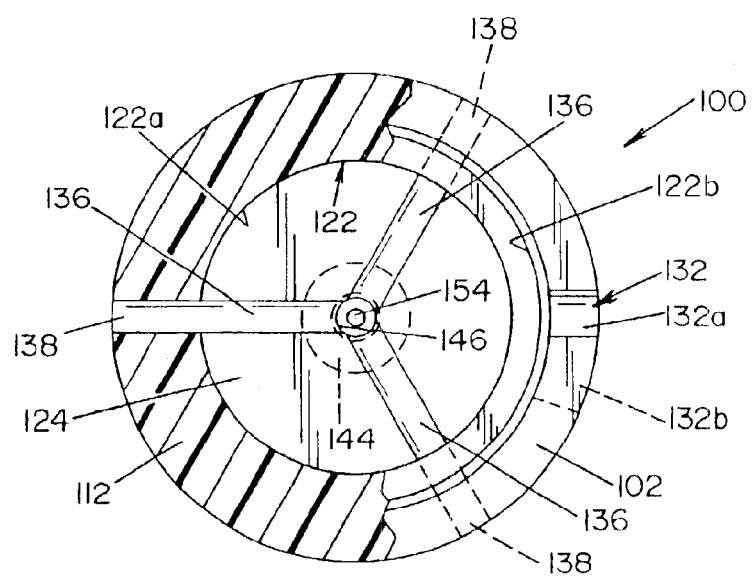
FIG. 4 is a sectional view taken along lines 4—4 of FIG. 2.

Inner surface 124 of end wall portion 114 includes three radially extending channels 136 that communicate with and form a part of openings 138 that extend through side wall portion 112 of second housing section 100, as best seen in FIGS. 3 and 4. Second housing section 100 includes a cylindrical boss 142 that is integrally formed on end wall portion 114. A threaded bore 144 is formed in boss 142, as best seen in FIGS. 2 and 3. An opening 146 extends through end wall portion 114 and communicates with bore 144. In the embodiment shown, opening 146 is a small, cylindrical passage communicating with the larger, threaded bore 144. A threaded plug 152 is dimensioned to be screwed into bore 144. A central orifice 154 extends through plug 152 and communicates with opening 146.

First and second housing sections 60, 100 are preferably formed of a polymeric material selected from the group consisting of polyolefins, and more preferably are formed of polypropylene. First and second housing sections 60, 100 are preferably formed of a polymeric material by means of a molding process. Pins 96 may be embedded within first housing section 60 during the molding process. First and second housing sections 60, 100 are generally symmetrical about an axis "A" that extends through fixture 10, as best seen in FIG. 1.

Referring now to the operation of fixture 10, a valve assembly 20 of the type heretofore described, is placed within fixture 10 for cleaning and deactivating during an automated cycle of a reprocessor (not shown). Fixture 10 is adapted to be mounted within the reprocessor. In the embodiment shown, fixture 10 is mounted to planar mounting plate 92 within the reprocessor by U-shaped pin 94. Fixture 10 is connected to a source of an anti-microbial fluid by means of a tube 88. Tube 88 is part of the fluid circulation system of the reprocessor, and anti-microbial fluid is forced through tube 88 during the microbial deactivation phase of the reprocessor.

With second housing section 100 removed from first housing section 60, valve assembly 20 is set within first housing section 60, as shown in FIG. 2. As illustrated in the drawings, valve stem 22 of valve assembly 20 extends into cavity 82 defined by first housing section 60. In this position, valve assembly 20 is in its normally "closed position" wherein spring 46 biases annular surface 28 on valve stem 22 and annular wall 36c of metal sleeve 36 into contact with each other, as shown in FIGS. 2 and 5. With valve assembly 20 positioned within first housing section 60, second housing section 100 is attached to first housing section 60. In this respect, leg portions 132a of slots 132 in second housing section 100 are aligned with pins 96 on first housing section 60. Second housing section 100 is then moved axially toward first housing section 60 with pins 96 entering leg portions 132a of slots 132. When pins 96 engage the bottom of slots 132, second housing section 100 is rotated angularly about axis "A" to move pins 96 into leg portions 132b and the closed end of L-shaped slots 132. As indicated above, cavity 106 defined by section 122a of surface 122 and surface 124 of end wall portion 114 is dimensioned to have a depth that is less than the length of cap 44 and collar 34, wherein cap 44 is forced into collar 34 when second housing section 100 is attached to first housing section 60, as illustrated in FIG. 3. When second housing section 100 is attached to first housing section 60, valve assembly 20 assumes an "opened position," wherein annular surface 28 on valve stem 22 is forced away from the surface of annular wall 36c. Valve assembly 20 is maintained in the open position, as shown in FIG. 3 during an automated cycle of a reprocessor. During such cycle, an anti-microbial fluid is forced through tube 88 into inner cavity 82 of first housing section 60. As indicated above, first and second housing sections 60, 100 are dimensioned such that a fluid-tight seal is formed between O-ring 72 of first housing section 60 and section 122b of inner surface 122 of second housing section 100. As a result, the anti-microbial fluid forced into inner cavity 82 of first housing section 60 is forced around and through valve assembly 20, as indicated by the arrows in FIGS. 3 and 6. The anti-microbial fluid is forced out of fixture 10 through openings 138 in second housing section 100 and through orifice 154 in plug 152, as indicated by the arrows in FIG. 3.

With valve assembly 20 held in an "opened position" as shown in FIG. 3, the interior and exterior surfaces of valve assembly 20 are exposed to the anti-microbial fluid as the fluid is forced through fixture 10 during an automated cycle of the reprocessor. Fixture 10 thus provides a means for cleaning interior surfaces of valve assemblies of endoscopes and other like devices.

While a single fixture 10 as shown in the drawings, it will be appreciated that most endoscopes include at least two valve assemblies 20. Accordingly, two fixtures 10 may be provided within the reprocessor to facilitate cleaning of valve assemblies 20 of an endoscope, together with the cleaning of the endoscope during an automated reprocessor cycle.

The foregoing description is a specific embodiment of the present invention. It should be appreciated that this embodiment is described for purposes of illustration only, and that numerous alterations and modifications may be practiced by Having described the invention, the following is claimed:

1. A fixture for holding a valve component in a washing system, said valve component having an open position and a normally closed position, said fixture comprising:

a first housing section and a second housing section, said sections being releaseably attachable to each other to form a fixture operable to hold said valve component in an opened position within said fixture;

said first housing section having an internal cavity dimensioned to receive a portion of said valve component through a first opening therein, said first housing section further having a fluid opening therethrough in communication with said internal cavity, said fluid opening being dimensioned to receive an anti-microbial fluid therethrough; and said second housing section having a second cavity dimensioned to receive a second portion of said valve component therein, said second housing having at least one fluid opening, said first housing section being attachable to said second housing section with said first cavity in said first housing section in registry with said second cavity in said second housing section to define a valve fixture holding chamber dimensioned to receive and hold said valve component in said opened position, said holding chamber dimensioned to allow fluid to pass around and through said valve component when an anti-microbial fluid is forced through said valve fixture holding chamber through said openings in said first and second housing sections.

2. A fixture as defined in claim 1, wherein said first and second housing sections are formed of a polymeric material.

3. A fixture as defined in claim 2, wherein said polymeric material is selected from the group consisting of polyolefins.

4. A fixture as defined in claim 3, wherein said polymeric material is polypropylene.

5. A fixture as defined in claim 1, wherein said first housing section is attached to said second housing section in a twist-lock fashion.

6. A fixture as defined in claim 1, wherein a fluid-tight seal is formed between said first housing section and said second housing section when said housing sections are attached to each other.

7. A fixture as defined in claim 1, wherein said fixture is attachable to a pressurized source of an anti-microbial fluid.

8. A fixture as defined in claim 1, wherein said valve assembly includes contacting surfaces when said valve assembly is in said normally closed position, said surfaces being spaced-apart when said valve assembly is in said open position.

9. A fixture for holding a valve assembly in an automated washing system, said valve assembly being movable between an opened position and a normally closed position, said fixture comprising:

first and second housing sections that are releaseably attachable to each other, said first housing section having a first internal cavity dimensioned to receive at least a portion of said valve component therein, and an opening communicating with said internal cavity;

said second housing section being releaseably attachable to said first housing section, said second housing section forming a fluid-tight attachment with said first housing section;

said first and second housing sections when attached to each other defining an internal chamber that is dimensioned to receive and hold said valve assembly in an opened position and to define a space around said valve assembly; and a first opening in said first housing section connectable to said source of an anti-microbial fluid to allow said chamber to be filled with said anti-microbial fluid.

10. A fixture as defined in claim 9, wherein said first and second housing sections are formed of a polymeric material.

11. A fixture as defined in claim 10, wherein said polymeric material is selected from the group consisting of polyolefins.

12. A fixture as defined in claim 11, wherein said polymeric material is polypropylene.

13. A fixture as defined in claim 9, wherein said first housing section is attached to said second housing section in a twist-lock fashion.

14. A fixture as defined in claim 9, wherein a fluid-tight seal is formed between said first housing section and said second housing section when said housing sections are attached to each other.

15. A fixture as defined in claim 9, wherein said fixture is attachable to a pressurized source of an anti-microbial fluid.

16. A fixture as defined in claim 9, wherein said valve assembly includes contacting surfaces when said valve assembly is in said normally closed position, said surfaces being spaced-apart when said valve assembly is in said open position.

17. A fixture for holding a valve assembly in an automated washing, system, said valve assembly being movable between an opened position and a normally closed position, said fixture comprising:

first and second housing sections that are releaseably attachable to each other, said housing sections defining an internal cavity dimensioned to hold said valve assembly in an opened position;

a fluid inlet in communication with said chamber, said fluid inlet attachable to a source of an anti-microbial fluid in said washing system; and a fluid outlet communicating with said chamber to allow said anti-microbial fluid to exit said fixture.

18. A fixture as defined in claim 17, wherein said first and second housing sections are formed of a polymeric material.

19. A fixture as defined in claim 18, wherein said polymeric material is selected from the group consisting of polyolefins.

20. A fixture as defined in claim 19, wherein said polymeric material is polypropylene.

21. A fixture as defined in claim 18, wherein said first housing section is attached to said second housing section in a twist-lock fashion.

22. A fixture as defined in claim 18, wherein a fluid-tight seal is formed between said first housing section and said second housing section when said housing sections are attached to each other.

23. A fixture as defined in claim 18, wherein said fixture is attachable to a pressurized source of an anti-microbial fluid.

24. A fixture as defined in claim 18, wherein said valve assembly includes contacting surfaces when said valve assembly is in said normally closed position, said surfaces being spaced-apart when said valve assembly is in said open position.

* * * * *